United States Patent [19]

Okumura et al.

[11] Patent Number: 5,852,050
[45] Date of Patent: Dec. 22, 1998

[54] PREPARATION FOR TREATING WOUNDS OR HEMORRHOIDS

[75] Inventors: Makoto Okumura; Toshiaki Okuda; Tsutomu Nakamura; Motoyuki Yajima, all of Kyoto, Japan

[73] Assignees: Kaken Pharmaceutical Co., Ltd.; Toray Industries Inc., both of Japan

[21] Appl. No.: 890,443

[22] Filed: Jul. 9, 1997

Related U.S. Application Data

[62] Division of Ser. No. 365,516, Dec. 27, 1994, Pat. No. 5,679,707, which is a division of Ser. No. 129,157, Nov. 30, 1993, Pat. No. 5,403,867.

[30] Foreign Application Priority Data

Feb. 7, 1992 [JP] Japan ........................... 4-22808
Jun. 24, 1992 [JP] Japan .......................... 4-189867

[51] Int. Cl.$^6$ ................................. A61K 31/557
[52] U.S. Cl. ............................ 514/468; 514/469
[58] Field of Search ........................ 514/468, 469

[56] References Cited

U.S. PATENT DOCUMENTS 5,401,768  3/1995  Ohno ........................ 514/468

OTHER PUBLICATIONS

Kouchi, J Vasc. Surg. 16 (2) 232 (1992).

*Primary Examiner*—Robert Gerstl
*Attorney, Agent, or Firm*—Nixon & Vanderhye

[57] ABSTRACT

The present invention relates to a preparation, particularly a topical preparation, for the therapy of wounds or hemorrhoids, which contains, as an active ingredient, at least one of prostaglandin $I_2$, prostaglandin $E_1$ and derivatives of these, particularly beraprost, a derivative of prostaglandin $I_2$, or a salt thereof, and a method of the therapy of wounds or hemorrhoids, which comprises administering the above active ingredient.

5 Claims, No Drawings

PREPARATION FOR TREATING WOUNDS OR HEMORRHOIDS

This is a division of application Ser. No. 08/365,516, filed Dec. 27, 1994 which is a division of Ser. No. 08/129,157 filed Nov. 30, 1993 now U.S. Pat. No. 5,403,867.

TECHNICAL FIELD

The present invention relates to a preparation for treating wounds or hemorrhoids

TECHNICAL BACKGROUND

Prostaglandin $I_2$ ($PGI_2$) and prostaglandin $E_1$ ($PGE_1$) are known to have a broad range of pharmacological activities such as high inhibition activity of platelet aggregation and high stimmulatory activity of vasolidating angiotelectasis, and it has been expected to apply these as a drug against peripheral blood circulation impairments. Since, however, $PGI_2$ and $PGE_1$ per se are chemically unstable, they are poor in retaining their pharmacological effects and it is difficult to apply them to practical use.

Beraprost which is a derivative of $PGI_2$ is chemically stable, and it has been therefore developed as an oral preparation for treating peripheral bloodstream impairments and is commercially available as a drug for the therapy of ischemic diseases caused by chronic arterial occlusion.

Meanwhile, it is known that most of wounds such as intractable skin ulcer including bedsore are caused by a failure in peripheral blood circulation. It is therefore desired to develop a drug for topical use since the topical administration thereof, if such is possible, causes lower side effects than systemic administration. However, there is not yet known any topical preparation for the therapy of wounds containing at least one of $PGI_2$, $PGE_1$ and derivatives thereof as an active ingredient.

On the other hand, hemorrhoids are generally classified into piles, anal fissure, periproctitis, perirectal abscess and anal fistula, and the preparations for the therapy thereof are largely classified into steroid-containing or no steroid-containing topical preparations against hemorrhoids and topical or systemic preparations against varicosis. The activity mechanism of these preparations for the therapy of hemorrhoids includes the activity for improving peripheral blood circulation, the activity for inhibiting thrombus formation, the anti-inflammatory activity and the activity for tissue restoration, and $PGI_2$, $PGE_1$ and derivatives thereof have all of these pharmaceutical activities, which suggests their usefulness as drugs for the therapy of hemorrhoids. However, their applications are not yet known.

It is an object of the present invention to provide a preparation, particularly a topical preparation, for the therapy of wounds or hemorrhoids, which contains at least one of $PGI_2$, $PGE_1$ and derivatives thereof as an active ingredient, and a method for the therapy of wounds or hemorrhoids which comprises administering the above active ingredient.

DISCLOSURE OF THE INVENTION

The present inventors have found that a composition which contains at least one of $PGI_2$, $PGE_1$ and derivatives thereof as an active ingredient and which is prepared by incorporating it into a pharmaceutically acceptable vehicle has a therapeutical effect on wounds or hemorrhoids.

The present inventors have found that beraprost which is a $PGI_2$ derivative or a salt thereof can be formed into a topical preparation suitable for symptoms of diseases since beraprost or a salt thereof is a powder which is chemically stable and soluble in water, and further that the preparation exhibits the high activity for promoting the healing of wounds by increasing the exudate amount and expediting the vascularization, granulation and epidermization.

The present inventors have also found that beraprost or a salt thereof has a high therapeutical effect on hemorrhoids when administered.

The present invention therefore relates to a preparation for the therapy of wounds or hemorrhoids (to be abbreviated as "present therapeutical preparation" hereinafter), which contains at least one of $PGI_2$, $PGE_1$ or derivatives thereof, particularly beraprost or a salt thereof, as an active ingredient and a pharmaceutically acceptable vehicle.

The present therapeutical preparation contains at least one of $PGI_2$, $PGE_1$ and derivatives thereof as an active ingredient. The derivative of $PGI_2$ includes beraprost, carbacyclin, iloprost, ciprosten, nileprost. cicaprost, CG4203, FCE22509, OP-41483, OP2507 and salts of these. Further, the derivatives of $PGI_2$ also includes salts of $PGI_2$ per se.

The salts of $PGI_2$ and its derivatives include, for example, pharmaceutically acceptable salts, i.e., alkali metal salts such as sodium salts and potassium salts, alkaline earth metal salts such as magnesium salts and calcium salts, ammonium salts, primary, secondary or tertiary amine salts and basic amino acid salts.

Of the above derivatives of $GPI_2$, particularly preferred are beraprost and its salts (particularly alkali metal salts such as sodium salt).

The above term "beraprost" is a generic name for (±)-(1R*, 2R*,3aS*,8bS*)-2,3,3a,8b-tetrahydro-2-hydroxy-1-[(E)-(3S*)-3-hydroxy-4-methyl-1-octen-6-ynyl]-1H-cyclopenta[b]benzofuran-5-butyric acid, and it includes not only a racemic modification but also d-form and l-form racemates.

The beraprost can be produced, for example, by the method described in JP-A-58-124778.

The derivative of $PGE_1$ includes misoprostol, ornoprostil, limaprost and salts of these. The derivative of $PGE_1$ also includes salts of $PGE_1$ per se.

The above salts include the above-described pharmaceutically acceptable salts such as alkali metal salts, alkaline earth metal salts, ammonium salts, amine salts, and basic amino acid salts.

The present therapeutical preparation is formed by incorporating the above active ingredient into a pharmaceutically acceptable vehicle.

The above vehicle includes, for example, water, ethanol, isopropanol, polyvinyl alcohol, polyvinylpyrrolidone, a carboxyvinyl polymer, sodium carboxymethylcellulose, sodium polyacrylate, sodium alginate, water-soluble dextran, sodium carboxymethylstarch, pectin, methylcellulose, ethylcellulose, propylcellulose, ethylmethylcellulose, hydroxypropylcellulose, xanthane gum, acacia, tragacanth gum, casein, albumin, gelatin, agar, chitin, sorbitol, maltitol, dextrin, lactose, sucrose, glucose, glycerin, diglycerin, triglycerin, propylene glycol, 1,3-butylenediol, polyethylene glycol, vaseline. paraffin, stearyl alcohol, glycerin monostearate, stearic acid. These vehicles are preferably used in combination as required.

The above vehicle is properly selected depending upon the form of the present therapeutical preparation.

The administration method of the present therapeutical preparation includes oral administration and non-oral administration. The dosage of the present therapeutical preparation differs depending upon the age, body weight and symptoms of a patient, route of administration and frequency of administration, while 0.1 μg to 100 mg thereof as one dosage, preferably 1 μg to 1 mg thereof as one dosage, is desirably administered once to four times per day.

For oral administration, it is used, for example, in the form of orally administrable, general pharmaceutical preparation such as a tablet, a capsule, a powder, granules or a solution. For non-oral administration, it is also used in the form of a preparation for injection, a suppository or a topical preparation.

When the present therapeutical preparation is used in the form of a topical preparation, it is used in the form of a general pharmaceutical preparation such as an ointment, gel, cream, lotion, a solution, an adhesive preparation, a spray solution, a tape preparation, a patch or a suppository.

When the present therapeutical preparation is used as a topical preparation, the content of the active ingredient in the preparation is 0.0001 to 10% by weight, preferably 0.001 to 1% by weight.

In the present specification, the term "therapy" should be understood in a broad sense, and it includes prevention in addition to therapy in its original sense. The present therapeutical preparation has its effect not only on the therapy of wounds or diseases but also on the prevention of these diseases.

PREFERRED EMBODIMENTS FOR WORKING THE INVENTION

The present invention will be further explained hereinafter by reference to Examples.

| [Preparation Example 1] Solution | |
|---|---|
| Beraprost sodium salt | 0.1 g |
| Macrogoal 400 | 5.0 g |
| Purified water | 85.5 g |
| Ethanol | proper amount |
| Total amount | 100.0 ml |

Macrogoal 400 is admixed with purified water. Then, beraprost sodium salt is dissolved, and ethanol is added until the total amount reaches 100 ml, whereby a solution is obtained.

| [Preparation Example 2] Ointment | |
|---|---|
| Beraprost sodium salt | 0.1 g |
| Macrogoal 400 | 55.0 g |
| Macrogoal 4000 | 39.9 g |
| Purified water | 5.0 g |
| Total amount | 100.0 g |

Macrogoal 400 and Macrogoal 4000 are dissolved at 80° C., and then while the mixture is fully kneaded under vacuum, the mixture is cooled to solidify it. The resultant solid is brought back to atmospheric pressure, and then a solution of beraprost sodium salt in purified water is added. The mixture is again fully kneaded under vacuum to obtain an ointment.

| [Preparation Example 3] Cream | |
|---|---|
| Beraprost sodium salt | 0.1 g |
| White petrolatum | 2.0 g |
| Liquid paraffin | 20.0 g |
| Stearyl alcohol | 4.0 g |
| Polyoxyl stearate 40 | 4.0 g |
| Glycerin monostearate | 4.0 g |
| Macrogoal 400 | 15.0 g |
| Purified water | 50.9 g |
| Total amount | 100.0 g |

Oil phase components (white petrolatum, liquid paraffin, stearyl alcohol and glycerin monostearate) are dissolved at 80° C. and water phase components (polyoxyl stearate 40, Macrogoal 400 and 45.9 g purified water) are dissolved at 80° C. and then added. The mixture is stirred for emulsification and solidification with cooling under reduced pressure. The reaction mixture is brought back to atmospheric pressure, and a solution of beraprost sodium salt in 5 g of purified water is added, and the mixture is fully kneaded under reduced pressure to obtain a cream.

| [Preparation Example 4] Tablet | |
|---|---|
| Beraprost sodium salt | 0.02 mg |
| Lactose | 64.98 mg |
| Corn starch | 25.00 mg |
| Crystalline cellulose | 7.50 mg |
| Hydroxypropyl cellulose | 2.20 mg |
| Magnesium stearate | 0.30 mg |
| Total amount | 100.00 mg |

A tablet containing 20 μg of beraprost sodium salt was obtained by the above prescription according to a conventional method.

| [Preparation Example 5] Suppository | |
|---|---|
| Beraprost sodium salt | 0.01 g |
| Witepsol H-15 | 99.99 g |
| Total amount | 100.00 g |

Witepsol H-15 was dissolved at 40° C., and then beraprost sodium salt was added. The mixture was stirred and supersonic-treated to form a uniform dispersion, and the dispersion was charged into suppository containers such that each container contained 2 g of the dispersion. The containers were cooled to obtain suppositories.

The effects of the present invention will be explained hereinafter by reference to Test Examples.

[TEST EXAMPLE 1]

Effect of Beraprost on Wound Healing in Full Sickness Wound Model of Diabetic Mice Whose Full-Thickness Skin Layer was Ablated 1. Test Method Hair on the backs of hereditary diabetic mice (C57BL/KsJ-dbm (db+/db+), male, 11 to 12 weeks of age, 6 mice per group) was removed one day before a test. The back portions of the mice were cleaned with ethanol under ether anesthesia, and circular full-thickness skin layer wounds (2 cm$^2$) were formed in the middle portions of the backs with surgical curved scissors.

Beraprost (sodium salt) as a test medicament was prepared in the form of a saline solution containing 20 % ethanol, and the saline solution was dropwise administered at a dosage of 5 μg/10 μl/cm$^2$×14 times (once per day for 14 days). As control, a solution (vehicle) containing no medicament was administered.

For evaluating the effects of the test medicament, the wound surfaces were traced on plastic sheets at intervals of 2–3 days, and measured for wound areas with a planimeter. The ratios of the wound areas to the area immediately after the skin ablation were calculated, and the numbers of days required for the visual completion of epidermization (complete healing) from the skin-removed wounds were used as indices.

Further, the degrees of the vascularization and granulation of wound surfaces were visually scored, and changes with the passage of days and side effects were observed.

Further, an exudate was collected 9 days after the skin ablation, and a mixture of the exudate with a saline solution used for washing the wound was measured for a leucocyte number through a microscope.

Further, the mice were sacrificed by ether anesthesia on 31th day, and skins of the wound portions were cut off and fixed with a 10% neutral buffer formalin solution. Then, paraffin sections, Hematoxyrin-Eosin-stained specimens and Masson trichrome-stained specimens were prepared according to conventional methods and observed through a microscope.

2. Test Results

The effects of the test medicaments on the change ratio of wound areas and the completion of healing were compared with those of the control group which had been administered with the vehicle, and Table 1 shows the results.

As shown in Table 1, the wound surfaces of the beraprost-administered group showed remarkable decreases from the sixth day after administration as compared with the vehicle-administered group, and they decreased to 24.4% and 0.1% on average on the 10th day and twenty-first day.

Further, the completion of healing was observed from the twenty-first day after administration, and all the mice were completely healed at least on the 24th day. The average period of days required for complete healing was 22 days, which showed a clear decrease as compared with that of the vehicle-administered group.

TABLE 1

Effect of beraprost on wound healing of diabetic mouse model whose full-thickness skin layer was ablated

| Test medicament | Days after administration (change ratio of wound area (%), mean ± S.E.) | | | | | | |
|---|---|---|---|---|---|---|---|
| | 3 | 6 | 8 | 10 | 13 | 15 | 17 |
| Vehicle | 105.2 ± 3.22 | 88.1 ± 1.67 | 75.6 ± 1.48 | 57.9 ± 3.01 | 32.1 ± 3.70 | 19.6 ± 4.97 | 14.2 ± 4.97 |
| Beraprost | 95.7 ± 2.50 | 66.2** ± 2.21 | 48.6** ± 2.11 | 24.4** ± 1.70 | 8.4** ± 1.65 | 2.5** ± 0.62 | 1.2** ± 0.43 |

| Test medicament | Days after administration | | | | Days until complete healing mean ± S.E. |
|---|---|---|---|---|---|
| | 21 | 24 | 28 | 31 | |
| Vehicle | 9.0 ± 6.43 | 7.3 ± 6.08 | 5.9 ± 5.41 | 5.2 ± 4.72 | 28.8 ± 1.13 |
| Beraprost | 0.1* ± 0.04 | 0** ± 0 | 0** ± 0 | 0** ± 0 | 22.0** ± 0.63 |

Significant difference from vehicle-administered group
*: P < 0.05
**: P < 0.01

When the vascularization and granulation on the wound surfaces were observed with the passage of days, the beraprost-administered group showed a clear expeditious progress in the vascularization and granulation as compared with the vehicle-administered group.

Table 2 shows the effects of beraprost on the amount of exudate and the number of infiltrated leucocyte on the wound surfaces (9 days after the administration). As shown in Table 2. the beraprost-administered group showed a clear increase in the amount of exudate and the number of infiltrated leucocyte as compared with the vehicle-administered group.

In the wound healing process, the epidermization rate increases in a wet wound surface as compared with a dry wound surface. Therefore, the increase in the amount of exudate observed at an early stage after the beraprost administration serves to promote the healing of wound.

Further, the increase in the number of infiltrated leucocyte promotes the process of recovery from inflammation. Further, since no weight difference was observed between the beraprost-administered group and the vehicle-administered group, no systemic side effects by the administration of beraprost was observed.

TABLE 2

Effects of beraprost on the amount of exudate and the number of leucocyte on wound surface (9 days after the administration)

| Test medicament | Amount of exudate (μl) mean ± S.E. | Number of infiltrated leucocycte (× 10$^4$ cells/site) mean ± S.E. |
|---|---|---|
| Vehicle | 0 ± 0 | 6.6 ± 3.58 |
| Beraprost | 36.6 ± 10.73** | 110.1 ± 31.66** |

Significant difference from vehicle-administered group
**: P < 0.01

Table 3 shows the histopathological data of wound portions observed 31 days after the skin ablation.

As shown in Table 3, the skin ablation portions of the vehicle-administered group had much high fiber growth (granulation) and exudate, and in a histological sense, the wound surfaces thereof were not completely covered with regenerated skin.

On the other hand, in the skin ablation portions of the beraprost-administered group, the whole areas were covered with regenerated skin and the exudate of the dermis disappeared. Further, in the fiber growth, the tissue showed transition to fibrosis, no formation of abnormal tissue or no scar of excess formation was shown, and normal wound healing was shown.

TABLE 3

Histopathological data of wound portions observed 31 days after the skin ablation.

| Tissue data | Test medicament | | Vehicle Number of cases in six mice | Beraprost Number of cases in six mice |
|---|---|---|---|---|
| Epidermis | Regeneration | − | 0 | 0 |
| | | + | 1 | 0 |
| | | ++ | 3 | 0* |
| | | +++ | 2 | 6 |
| | Hypertrophy | + | 1 | 1 |
| Dermis. Subcutaneous tissue | Granulation | − | 0 | 4 |
| | | + | 4 | 2* |
| | | ++ | 2 | 0 |
| | Exudate | − | 1 | 5* |
| | | + | 5 | 1 |
| | Fibrosis | − | 2 | 0 |
| | | + | 1 | 0* |
| | | ++ | 3 | 2 |
| | | +++ | 0 | 4 |

Scores of histological data
−: Not affected
+: Low degree
++: Intermediate degree
+++: High degree
Significant difference from control group
(H test) *: $P < 0.05$

[TEST EXAMPLE 2]

Prevention and Therapy Effects on Experimental Hemorrhoids Model in Rats

1. Test Materials

1) Method of preparation of inflammation-inducing agent containing croton oil

A mixture of 1 volume of distilled water, 4 volumes of pyridine, 5 volumes of ethyl ether and 10 volumes of a 3% croton oil ethyl ether solution was used. The distilled water and a small amount of ethyl ether were added to, and blended with, the pyridine, and the 3% croton oil ethyl ether solution was added. Further, the remaining ethyl ether was added, and the mixture was vigorously stirred to prepare an inflammation-inducing agent containing croton oil. This solution was prepared just before the test, and stored with ice cooling during the test.

2) Method of preparation of test solutions and dosages

Beraprost (sodium salt) was dissolved in distilled water to prepare a solution for oral administration and dissolved in a saline solution to prepare a solution for intrarectal administration.

In the test of effects on the prevention of hemorrhoids, the dosage for oral administration was 0.1, 0.3 or 1.0 mg/kg, and the dosage for intrarectal administration was 0.01, 0.03, 0.1, 0.3 or 1.0 mg/kg. In the tests of effects on the therapy of hemorrhoids, the dosage for oral administration was 0.1 mg/kg, and the dosage for intrarectal administration was 0.03 mg/kg. Further, the dosage of the solution for oral administration was 10 ml/kg, and the dosage of the solution for intrarectal administration was 100 $\mu$l/kg.

3) Animal Used

Male SLC: Wistar rats of 7 to 8 weeks of age (Nippon SLC K.K.) were fasted overnight so that the rats had a weight of 167 to 200 g. Seven to 8 rats were used as one group.

2. Test Method

In the test of prevention of hemorrhoids, beraprost was orally or intrarectally administered, and 30 minutes after the administration, 100 $\mu$l of the inflammation-inducing agent containing croton oil was infiltrated into the tampon of a swab and the tampon was inserted into the anus of each rat under no anesthesia for 10 seconds to induce inflammation.

Three hours after the induction of inflammation, the rats were sacrificed by bleeding under anesthesia with ethyl ether, and a rectum-anus portion was taken from each rat such that it was exactly 20 mm long from a circular hairline on the anus epithelium, and measured for a weight.

Further, in the intrarectally administered group, the isolated rectum-anus portion was fixed with a 10% neutral buffer formalin solution, and paraffin sections, Hematoxyrin-Eosin-stained specimens and Phosphotungstic acid hematoxyin-stained specimens were prepared according to conventional methods. Then, these were observed and their photographs were taken through an optical microscope The histological data obtained by the intrarectal administration of beraprost were examined.

In the test of effects on the therapy of hemorrhoids, inflammation was induced with an inflammation-inducing agent containing croton oil in the same manner as in the test of effects on the prevention. Beraprost was administered twice a day in the morning and evening for 4 days, and the administration was started one day after the induction of inflammation. Rectum-anus portions isolated after 5 days in the same manner as in the test of effects on prevention were measured for a weight.

In addition, distilled water alone was administered to the control group for oral administration, and a saline solution (vehicle) alone was administered to the control group for intrarectal administration. Further, for comparison, a non-treated group which was neither treated with the inflammation-inducing agent containing croton oil and nor treated with a medicament and which was neither administered with distilled water nor administered with a saline solution was tested in the same manner.

3. Statistical Procedure

For the effect of beraprost on the weight of the rectum-anus portion, the difference from the control group was determined according to Student's t test, and for the histological data, the difference from the control group was determined according to Kruskal-Wallis H test. Further, the inhibition ratio was calculated on the basis of the rectum-anus portion average weight of each group by the following equation.

Inhibition ratio (%)={1−[medicament-administered group−non-treated group)/(control group−non-treated group)]}×100

4. Test Results

Table 4 shows the results of oral administration of beraprost on the prevention of hemorrhoids.

The average value of the rectum-anus portion weights of the non-treated group was 165.1 mg, while that of the control group which had been administered with the vehicle alone and then treated with the inflammation-inducting agent was 353.2 mg, and showed a significant (P<0.01) increase as compared with the non-treated group.

Under the above conditions, clear swelling inhibition activity depending upon the dosage of beraprost was shown on the groups which had been administered with 0.1 to 1.0 mg/kg of beraprost.

TABLE 4

Effect of orally administered beraprost on the prevention of hemorrhoids

| Test group | Dosage (mg/kg) | Number of rats | Wet weight of anus-rectum average ± standard error (mg) | Inhibition ratio (%) |
|---|---|---|---|---|
| Control group (distilled water) | — | 8 | 353.2 ± 9.20 | — |
| Beraprost | 0.1 | 8 | 307.1 ± 5.87** | 24.5 |
|  | 0.3 | 8 | 292.5 ± 11.28** | 32.3 |
|  | 1.0 | 8 | 279.3 ± 8.32** | 39.3 |
| Non-treated | — | 7 | 165.1 ± 6.72** | — |

Significant difference from control group (t test)
**: P < 0.01

Table 5 shows the results of intrarectal administration of beraprost on the prevention of hemorrhoids.

As compared with the increase in the rectum-anus portion weight caused by the inflammation-inducing agent, a significant inhibition activity was shown (P<0.05 to 0.01) on the groups which had been administered with 0.01 to 1.0 mg/kg of beraprost, and the effect was the largest on the group which had been administered with 0.03 mg/kg of beraprost.

TABLE 5

Effect of intrarectally administered beraprost on the prevention of hemorrhoids

| Test group | Dosage (mg/kg) | Number of rats | Wet weight of anus-rectum average ± standard error (mg) | Inhibition ratio (%) |
|---|---|---|---|---|
| Control group (Saline solution) | — | 8 | 349.1 ± 10.89 | — |
| Beraprost | 0.01 | 8 | 303.3 ± 6.25** | 22.9 |
|  | 0.03 | 8 | 277.3 ± 12.88** | 35.8 |
|  | 0.1 | 8 | 288.7 ± 5.63** | 30.1 |
|  | 0.3 | 8 | 299.7 ± 9.74** | 24.6 |
|  | 1.0 | 8 | 308.0 ± 14.51* | 20.5 |
| Non-treated | — | 7 | 148.4 ± 5.50** | — |

Significant difference from control group (t test)
*: P < 0.05
**: P < 0.01

Table 6 shows the test results on the effect of intrarectally administered beraprost on histological data.

In the control group which had been administered with a saline solution alone, the rectum showed bleeding, necrosis and peeling of a mucosal layer, which were caused by the inflammation-inducing agent, in a broad range (total length from anus transitional portion, 8.0±0.51 mm on average), and further, swelling and inflammatory cell infiltration into submucosal tissue were outstanding. Further, the mucosa and submucosal tissue showed a number of congested and dilated bloods capillaries (22.4±2.54 on average) having red thrombus (total number, observed in blood vessels having a diameter of at least 500 μm present in an entire field of vision).

On the other hand, in the group which had been administered with 0.03 mg/kg of beraprost, the range of bleeding, necrosis and peeling of mucosal layer was significantly (P<0.01) inhibited (5.4±0.19 mm on average). Further, the degrees of swelling and inflammatory cell infiltration lowered, the mucosal epithelial cell nucleus was more densely stained than in a normal portion, and cells which appeared to be in an active state were distinctly observed. Moreover, the degree of congestion was lowered, and the number of blood vessels having red thrombus significantly (P<0.01) decreased (6.8±2.35 on average).

TABLE 6

Histopathological data in intrarectal administration of beraprost

| Data of rectum | | | Control (saline solution) | Beraprost 0.3 mg/kg |
|---|---|---|---|---|
| Mucosa | Bleeding, Necrosis, Peeling (total length from anus transition portion: mm) Note 1 | | 8.0 ± 0.51 | 5.4 ± 0.19** |
|  | Red thrombus (number of thrombus) Note 1 | | 22.4 ± 2.54 | 6.8 ± 2.35** |
|  | Epithelium | − | 1 | 0 |
|  | Activation | + | 7 | 2 XX |
|  |  | ++ | 0 | 6 |
|  | Congestion | + | 2 | 8 XX |
|  |  | ++ | 6 | 0 |
| Submucosa | Swelling | ++ | 2 | 8 XX |
|  |  | +++ | 6 | 0 |
|  | Inflammatory cell infiltration | + | 1 | 5 X |
|  |  | ++ | 7 | 3 |

Significant difference from control group (t test)
**: P < 0.01
Significant difference from control group (H test)
X: P < 0.05. XX: P < 0.01
Note 1: Average ± standard error
Scores −: No change, +: Low degree, ++: Intermediate degree. +++: High degree
Number of rats: 8

It is seen from the above results that beraprost when orally and intrarectally administered in the tests of effects on the prevention of hemorrhoids clearly inhibits the swelling caused in a rectum-anus portion by the inflammation-inducing agent containing croton oil and exhibits remarkable effects in histopathological data.

Table 7 shows the results of orally and intrarectally administered beraprost on the prevention of hemorrhoids.

In the results, both when orally administered at a dosage of 0.1 mg/kg and when intrarectally administered at a dosage of 0.03 mg/kg, beraprost has exhibited the significant (P<0.05) activity for inhibiting the swelling.

TABLE 7

Effects of orally and intrarectally administered beraprost on therapy of hemorrhoids

| Test group | Dosage (mg/kg) | Administration route | Number on rats | Wet weight of anus-rectum average ± standard error (mg) | Inhibition ratio (%) |
|---|---|---|---|---|---|
| Control (distilled water) | — | p.o | 7 | 457.9 ± 24.51 | — |

TABLE 7-continued

Effects of orally and intrarectally administered beraprost on therapy of hemorrhoids

| Test group | Dosage (mg/kg) | Administration route | Number on rats | Wet weight of anus-rectum average ± standard error (mg) | Inhibition ratio (%) |
|---|---|---|---|---|---|
| Beraprost | 0.1 | p.o. | 7 | 380.7 ± 23.74* | 27.1 |
|  | 0.03 | i.r. | 7 | 368.5 ± 27.35* | 31.4 |
| Non-treated | — | — | 7 | 173.0 ± 6.13** | — |

Significant difference from control group (t test)
*: $P < 0.05$. **: $P < 0.01$
Administration route p.o.: orally, i.r.: intrarectally

EFFECTS OF THE INVENTION

According to the present invention, there have been provided a useful preparation for the therapy of wounds or hemorrhoids, which exhibits the high activity for promoting the therapy of wounds and the high therapeutical effect on hemorrhoids, particularly a topical preparation for the therapy of wounds or hemorrhoids, and a method for the therapy of wounds or hemorrhoids.

We claim:

1. A method for treating wounds, which comprises administering orally to a person in need of same an effective amount of at least one prostaglandin $I_2$ compound.

2. A method according to claim 1, wherein the prostaglandin $I_2$ compound is beraprost, carbacyclin, iloprost, ciprosten, nileprost, cicaprost, CG4203, FCE22509, OP41483, OP2507 or a salt thereof.

3. A method according to claim 2, wherein the salt is selected from alkali metal salts, alkaline earth metal salts, primary, secondary or tertiary amine salts, and basic amino acid salts.

4. A method according to claim 1, wherein the compound is administered at a dosage of 0.1 μg to 100 mg once to four times per day.

5. A method according to claim 4, wherein the dosage is 0.1 μg to 1 mg.

* * * * *